(12) United States Patent
Zhou et al.

(10) Patent No.: US 9,700,230 B2
(45) Date of Patent: Jul. 11, 2017

(54) ENHANCED FAT SATURATION IN MYOCARDIAL INFARCTION MRI

(75) Inventors: Xiangzhi Zhou, Vernon Hills, IL (US); Mitsue Miyazaki, Mount Prospect, IL (US)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1162 days.

(21) Appl. No.: 13/598,435

(22) Filed: Aug. 29, 2012

(65) Prior Publication Data

US 2014/0062474 A1    Mar. 6, 2014

(51) Int. Cl.
 *A61B 5/055* (2006.01)
 *A61B 5/00* (2006.01)
 *G01R 33/56* (2006.01)

(52) U.S. Cl.
 CPC ............ *A61B 5/055* (2013.01); *A61B 5/0044* (2013.01); *G01R 33/5607* (2013.01)

(58) Field of Classification Search
 USPC .......................... 324/300–322; 600/407–435; 382/128–131
 See application file for complete search history.

(56) References Cited

U.S. PATENT DOCUMENTS 7,323,871 B2 * 1/2008 Foo .............................. 324/307
9,030,201 B2 * 5/2015 Rehwald ............ G01R 33/4828
 324/307

2007/0007958 A1 * 1/2007 Foo ............................... 324/307
2008/0081986 A1 * 4/2008 Slavin .................... A61B 5/055
 600/410

(Continued)

FOREIGN PATENT DOCUMENTS

JP    5-200012    8/1993
JP    2008-086343    4/2008

(Continued)

OTHER PUBLICATIONS

Simonetti, et al., "An Improved MR Imaging Technique for the Visualization of Myocardial Infarction," Radiology, vol. 218, pp. 215-223 (Jan. 2001).

(Continued)

*Primary Examiner* — Melissa Koval
*Assistant Examiner* — Tiffany Fetzner
(74) *Attorney, Agent, or Firm* — Nixon & Vanderhye P.C.

(57) ABSTRACT

MRI k-space data is acquired for a patient ROI during data acquisition sequences including a nuclear magnetic resonance (NMR) signal readout period using a late gadolinium enhanced (LGE) data acquisition sequence including at least one fat-specific RF NMR magnetization inversion pulse imposed (a) after a water-specific RF NMR magnetization inversion pulse timed to cause a substantial null in NMR magnetization of normal tissue protons near a center of the readout period and (b) before the readout period center, which fat-specific inversion pulse is also timed to cause a substantial null in NMR magnetization of fat tissue protons near the readout period center. The acquired MR image data is reconstructed into a contrast enhanced LGE image of tissues within the ROI but having substantially suppressed normal and fat components therein.

10 Claims, 5 Drawing Sheets

(56) References Cited

U.S. PATENT DOCUMENTS

| | | | | |
|---|---|---|---|---|
| 2010/0194388 | A1 | 8/2010 | Kitane et al. | 324/309 |
| 2012/0194193 | A1* | 8/2012 | Rehwald | G01R 33/4828 |
| | | | | 324/318 |
| 2013/0274592 | A1* | 10/2013 | Shin et al. | 600/420 |
| 2014/0062474 | A1* | 3/2014 | Zhou et al. | 324/309 |

FOREIGN PATENT DOCUMENTS

| | | |
|---|---|---|
| JP | 2009-279202 | 12/2009 |
| WO | 2012/060192 A1 | 5/2012 |

OTHER PUBLICATIONS

Ordovas, et al., "Delayed Contrast Enhancement on MR Images of Myocardium: Past, Present, Future," Radiology, vol. 261, No. 2, pp. 358-374 (Nov. 2011).

Vogel-Claussen, et al., "Delayed Enhancement MR Imaging: Utility in Myocardial Assessment," RadioGraphics, vol. 26, No. 3, pp. 795-810 (2006).

* cited by examiner

ENHANCED FAT SATURATION IN MYOCARDIAL INFARCTION MRI

FIELD

The subject matter below relates generally to magnetic resonance imaging (MRI) apparatus and process. In particular, the MRI apparatus and method described below involve fat saturation/suppression in late gadolinium enhanced (LGE) myocardial infarction MRI.

DETAILED DESCRIPTION

Figure 1:
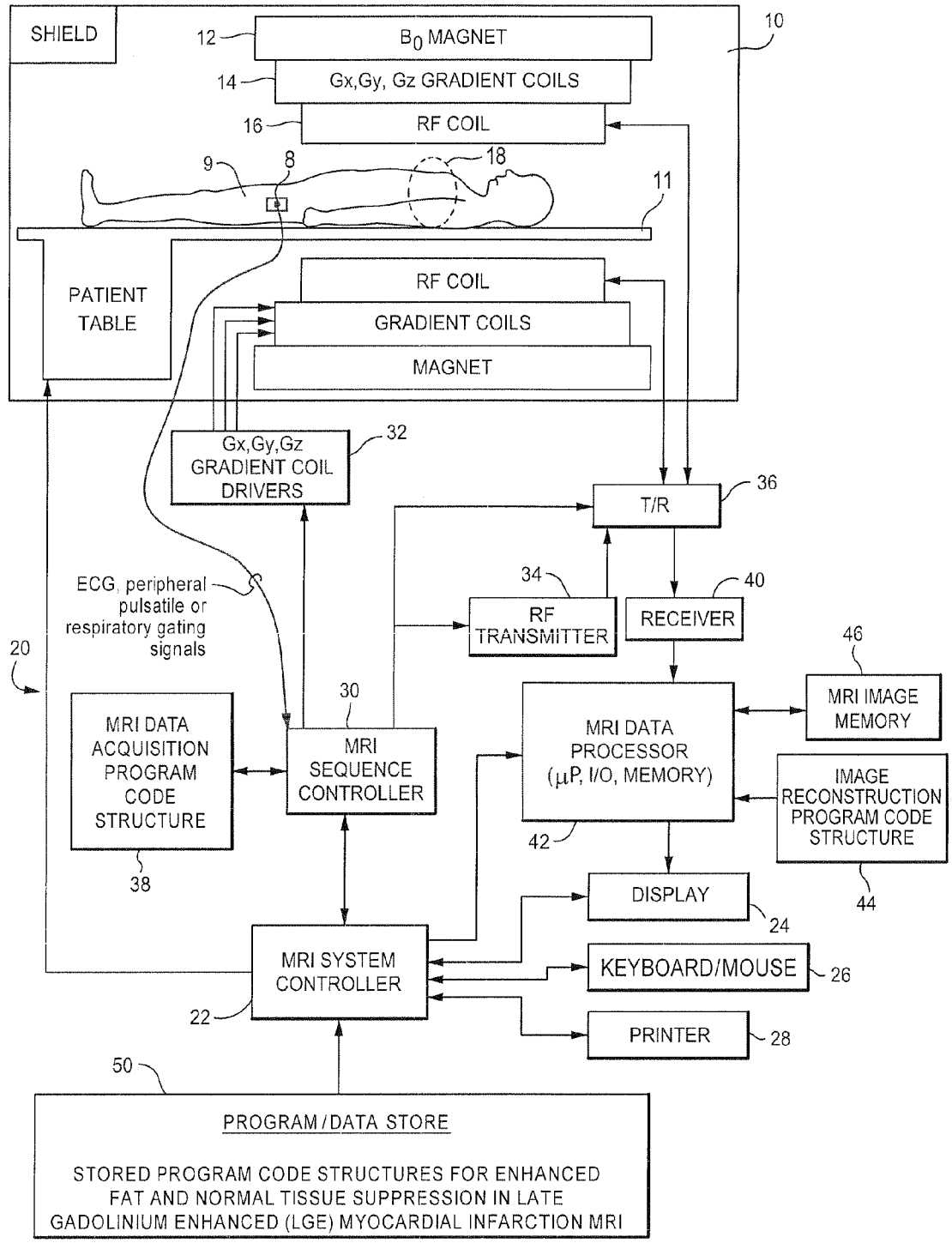
FIG. 1 is a high-level schematic block diagram of an exemplary MRI system embodiment configured to provide enhanced fat saturation/suppression in late gadolinium enhanced (LGE) myocardial infarction MRI.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field Bo magnet 12, a Gx, Gy and Gz gradient coil set 14 and an RF coil assembly 16. Along the horizontal axis of this cylindrical array of elements is an imaging region 18 shown as substantially encompassing the anatomy of interest for a patient 9 (e.g., the heart for cardiac MRI) supported by a patient bed or table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the Gx, Gy and Gz gradient coil drivers 32, as well as RF transmitter 34 and transmit/receive switch 36 (if the same RF coil is used for both transmission and reception). As those skilled in the art will appreciate, many different types of RF coils (e.g., whole body coils, surface coils, birdcage coils, coil arrays, etc.) may be employed to transmit and/or receive RF signals to/from the region of interest (ROI) in the imaging volume. As will also be appreciated, one or more suitable physiological transducers may be affixed to the patient's body to provide ECG (electrocardiogram), respiratory and/or peripheral pulsatile gating signals to the MRI sequence controller 30. The MRI sequence controller 30 also has access to suitable program code structure 38 for implementing MRI data acquisition sequences already available in the repertoire of the MRI sequence controller 30—e.g., to generate MR images using operator and/or system inputs defining particular MRI data acquisition sequence parameters.

The MRI system 20 includes an RF receiver 40 providing input to data processor 42 so as to create processed image data which may be sent to display 24. The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for enhanced fat saturation/suppression in late gadolinium enhanced (LGE) myocardial infarction MRI, a related graphical user interface (GUI), operator inputs to same, etc.) are stored in computer readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those skilled in the art will appreciate, the FIG. 1 depiction is a very high level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged region space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images. Specifically, we have discovered methods which better suppress fat signal components in late gadolinium enhanced (LGE) myocardial infarction magnetic resonance imaging (MRI).

The new methods can separately invert water and fat signals in LGE-MRI so as to better depict substantially only infarcted myocardium tissues. That is, both healthy myocardium and fat tissues can be substantially nulled during an active data acquisition portion of the overall MRI data acquisition sequence so that substantially only infarcted myocardial signal is acquired and used for MR image producing purposes.

It is believed that the new techniques herein presented can perform better fat suppression than is possible with a conventionally used FatSat (Fat Saturation) pulse approach.

In late gadolinium enhanced (LGE) myocardial infarction (MI) magnetic resonance imaging (MRI), T1 weighted contrast is generated between healthy myocardium and infarcted myocardium. The T1 difference is caused by gadolinium trapped in infarcted myocardium—and that reduces the water spin-lattice relaxation time (T1) compared to normal myocardium. In LGE MI imaging, the T1 contrast is maximized by inverting water magnetization and allowing healthy myocardium and infarcted myocardium to recover at their respective different rates. MRI data acquisition is triggered when the healthy myocardium magnetization is zero and while infarcted myocardium remains with a positive magnetization (e.g., see FIG. 2). Therefore, in an LGE image, healthy myocardium appears to be dark, and infarcted myocardium appears to be bright.

Figure 2:
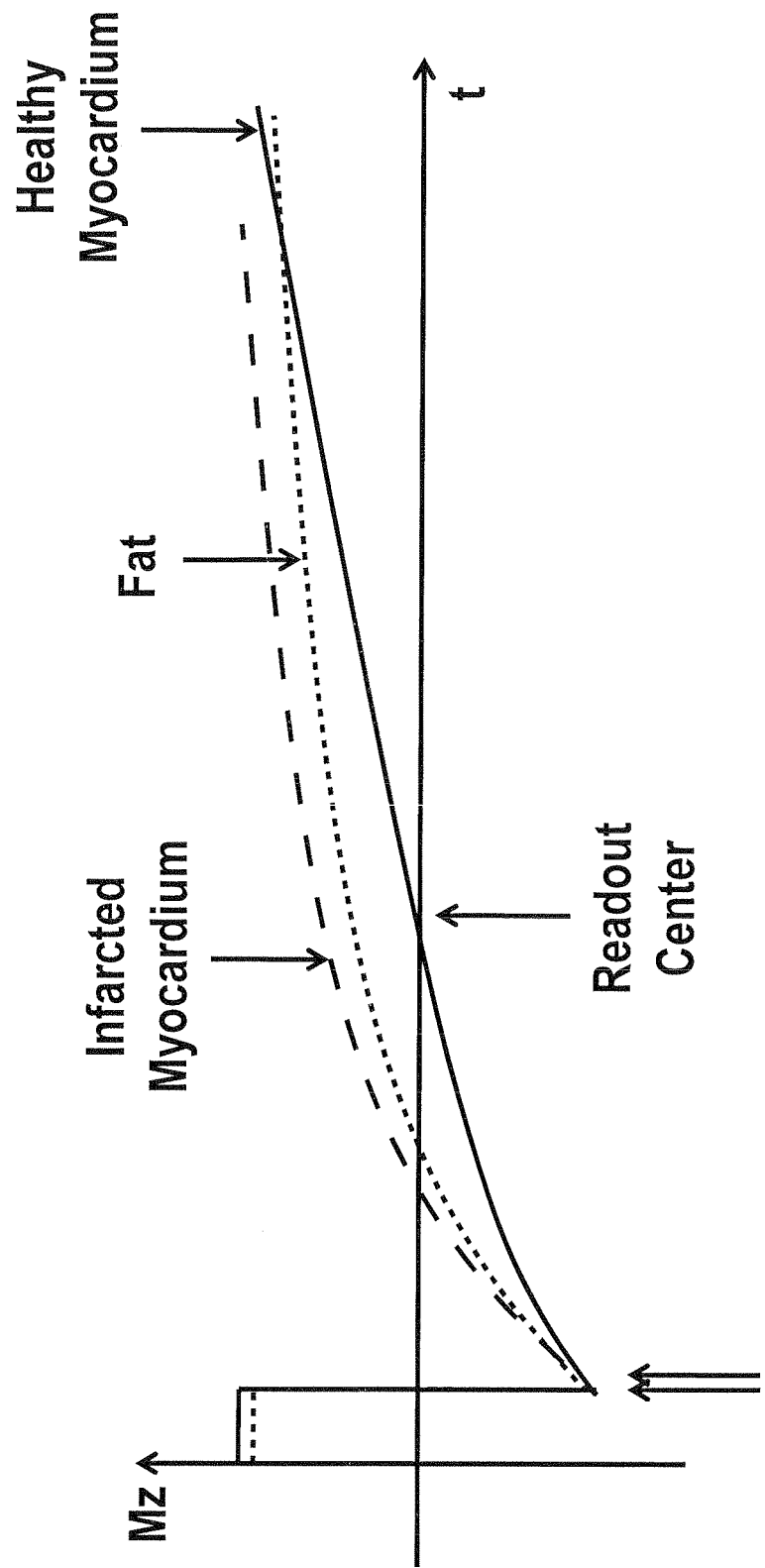
FIG. 2 depicts a typical prior art LGE MRI data acquisition timing diagram.

However, fat signal is also bright in LGE images if patients have fat infiltration to the myocardium or have pericardial fat (e.g., see also FIG. 2). This may cause diagnosis inaccuracy if the infarct zone cannot be distinguished from fat. Thus, fat suppression is necessary in LGE MI imaging.

Our new approach can generate T1 weighted water signal from substantially only infarction myocardium—by separately suppressing acquired NMR signals from each of fat and healthy myocardium. In one method, we use a water-specific excitation pulse to invert substantially only water magnetization, wait a certain amount of time, and then invert substantially only fat magnetization using SPIR (Spectral Pre-saturation with Inversion Recovery) or double FatSat. The SPIR should happen at a delay time so that thereafter the fat signal is nulled concurrently with the healthy myocardial signal. Active k-space data acquisition takes place during the time when both fat signal and healthy myocardial signal are substantially nulled, and yet when infarcted myocardium has substantial detectable magnetization Mz—thus leading to a myocardium infarct image with better suppression of both fat and normal tissues.

Fat suppression can be realized by inverting the fat signal and waiting a predetermined fat inversion time (TI) until the fat signal is nulled. Current fat suppression methods used in LGE MI imaging include:

1. STIR (Short Tau Inversion Recovery): invert magnetization and acquire water signal when fat signal is nulled.
2. CHESS (CHEmical Shift Selective): a fat selective RF pulse is used to saturate only the fat signal
3. SPIR (Spectral Pre-saturation with Inversion Recovery): invert only fat magnetization and acquire water signal when fat signal is nulled.

In LGE-MRI, the first pulse is non-selective so it inverts all magnetizations including fat and myocardium. During magnetization recovery, infarcted myocardium data is acquired when the healthy myocardium is at its null point and thus the contrast is hopefully maximized to differentiate normal from infarcted myocardium. However, fat signal may both appear together with infarct myocardium. Thus, a method is needed that can either (a) invert water and fat separately for the first inversion, or (b) a method to suppress fat signal efficiently if the first inversion is non-selective.

Current fat suppression methods use a non-selective inversion pulse for the first inversion, so both fat and water signals are inverted, after which:

1. STIR technique does not perform well since the inversion is non-selective so it will invert both water and fat signals again, and it cannot simultaneously null both fat and healthy myocardial signals.
2. CHESS or SPIR can select fat signal to invert, but at the time when the fat magnetization is inverted, the fat magnetization is probably not fully recovered from the first inversion, and it can be either negative or positive. This will reduce fat suppression efficiency and sometimes fat suppression may fail.

In an exemplary embodiment, a technique is used that can generate T1 weighted water signal from only infarction tissue while suppressing both fat and healthy myocardium signals. In a first technique, a water excitation pulse is used to invert only water magnetization. After an amount of wait time TI1, fat magnetization is inverted using SPIR. SPIR should occur at TI1 so that after TI2, fat signal is nulled together with healthy myocardial signal (e.g., see FIG. 3). In a second technique, a non-selective IR pulse (as in the prior art) is used to invert both fat and myocardial signal. However, within the TI of healthy myocardium, a series of variable flip angle CHESS/SPIR pulses are applied to suppress fat signal (e.g., see FIG. 4).

For both techniques, data acquisition takes place when both fat signal and healthy myocardium signal are substantially nulled, and infarcted myocardium has positive magnetization. As those in the art will appreciate, the active data acquisition period requires a finite time and therefore only part of the data acquisition period will occur when the fat and healthy tissue signals are actually nulled. The desire is to have the centrally located k-space data lines acquired when the fat and normal myocardium signals are substantially nulled, because the central k-space lines provide greater image contrast than other data lines in k-space.

The phase encoding order during MRI k-space signal acquisition sequences should be adjusted to insure that centrally located k-space data lines (which produce most contrast in a final reconstructed image) are acquired when both fat and healthy myocardial signal are substantially nulled. For linear ordering of phase encoding increments, the active data acquisition (read out) period should start before fat and normal tissue signals pass their mutual nulling point (e.g., so that central k-space lines are acquired at a time when the fat and normal tissue signals are substantially nulled). If the readout time period is too long, then centric ordering of phase encoding increments should be used and the active data acquisition period can begin substantially at the normal & fat tissue signal nulling point (because the first few acquired lines of data will now be located in the center of k-space). Accordingly, for an LGE FatSat implementation, linear phase increment ordering can be used as a default option. If the readout time is deemed too long, a switch can be made to centric phase increment ordering.

Figure 3:
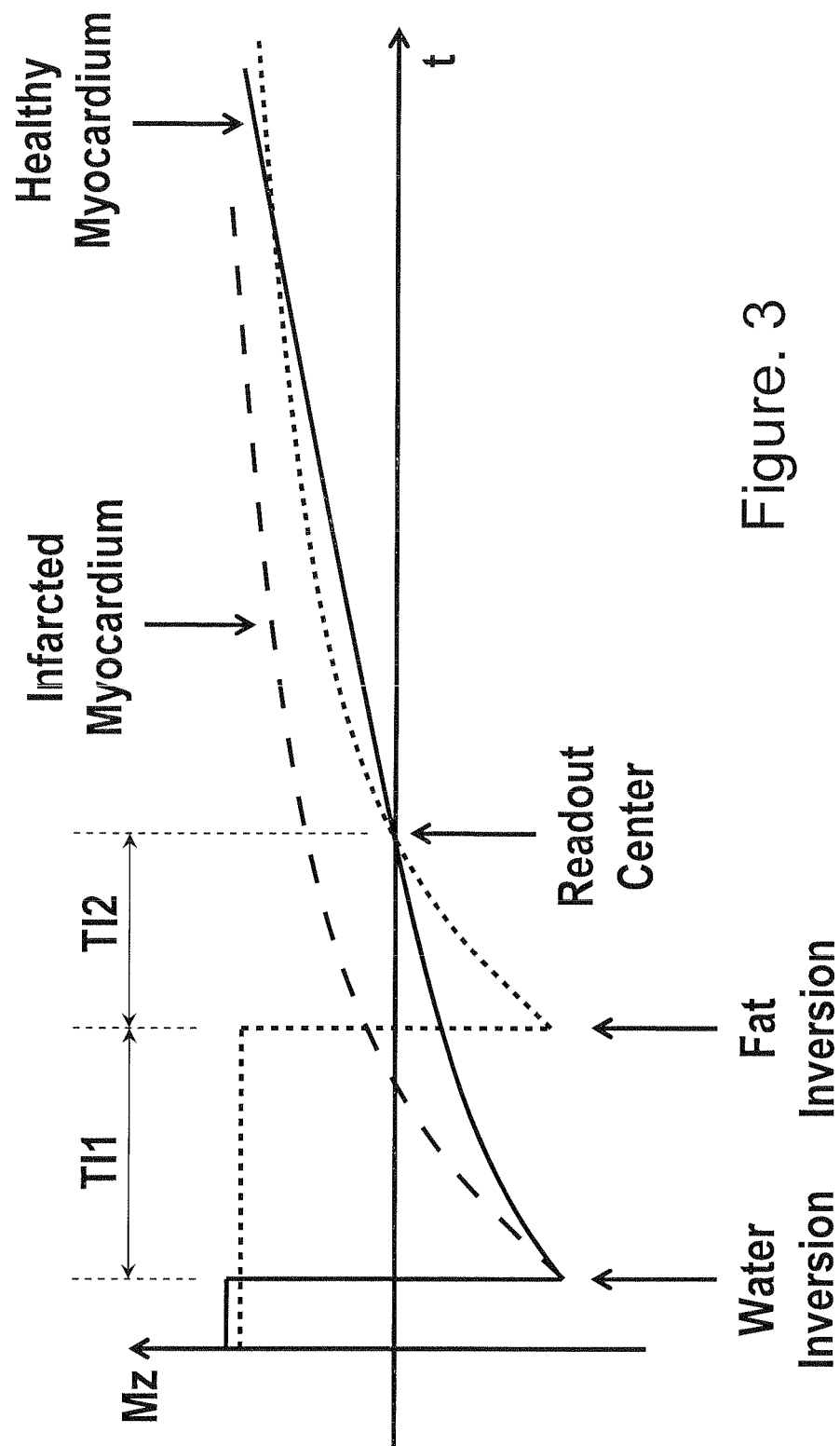
FIG. 3 depicts a modified LGE MRI data acquisition timing cycle including a first method of fat suppression.

As seen in FIG. 3 (embodiment 1), there are three blocks of time:

1. water inversion block
2. fat inversion block
3. readout block.

The timing of the above blocks in this embodiment is as follows:

The time between the water inversion pulse and the fat inversion pulse is TI1.

The time between the fat inversion pulse and readout center is TI2, which is equal to Fat TI.

The healthy myocardium TI is the time between water inversion and readout center, which is equal to TI1+TI2.

Water inversion can be realized by:

1. binomial composite pulses (90-tau-90 or 45-tau-90-tau-45 or 22.5-tau-67.5-tau-67.5-tau-22.5) to invert water magnetization to −Mz and keep fat signal at +Mz. Tau depends on field strength; at 1.5 T tau=2.2 ms, and at 3.0 T tau=1.1 ms.

2. water selective RF pulse with 180° flip angle.

Fat suppression can be realized by:

1. SPIR: to invert fat signal only
2. Fat selective CHESS: to saturate fat signal only
3. Double Fat Suppression (DFS): combined SPIR and CHESS pulse to effectively suppress fat signal.

Readout can use:

1. bSSFP (balanced Steady State Free Precession)
2. GRE (GRadient Echo).

Figure 4:
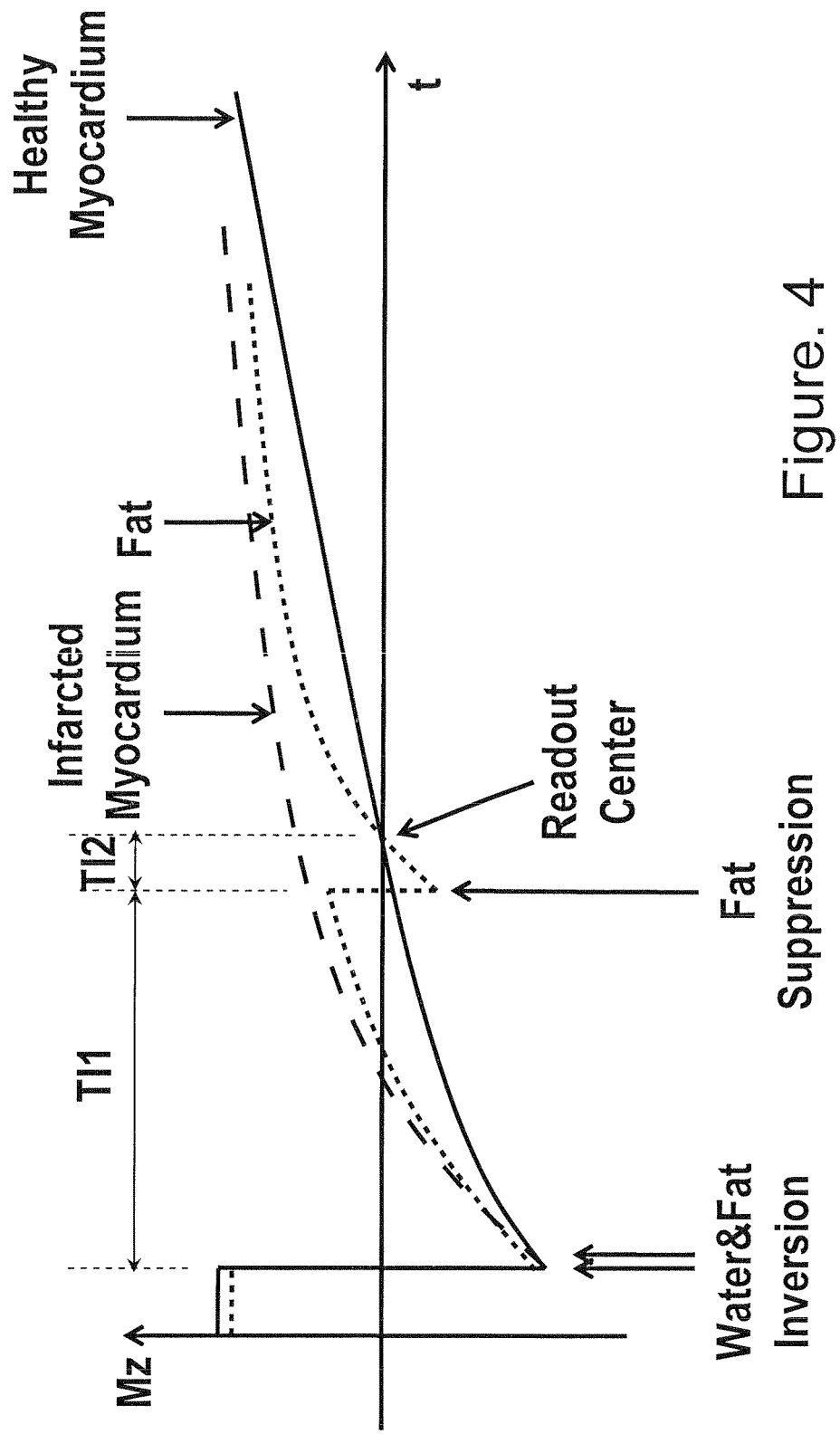
FIG. 4 is similar to FIG. 3, but depicts a second method of fat suppression in an LGE MRI data acquisition timing diagram.

As seen in FIG. 4 (embodiment 2), this exemplary embodiment also has three blocks:

1. water and fat inversion block
2. fat suppression (saturation or inversion) block
3. readout block.

The timing of the above blocks is as follows:

The time between the non-selective pulse and the fat inversion pulse is TI1.

The time between the fat inversion pulse and readout center is TI2.

Healthy myocardium TI is the time between the non-selective inversion pulse and readout center, which is equal to TI1+TI2.

TI1 and TI2 can be calculated because healthy myocardium T1 and fat T1 are known (e.g., at 1.5 T or 3.0 T).

In this method, water and fat inversion can be realized by a non-spatially selective inversion pulse as in the prior art.

Fat suppression can be realized by:

1. SPIR to invert fat signal only at TI1 so that, at TI2, the fat signal is nulled. The TI1 and TI2 values can be calculated with known healthy myocardium T1 and fat T1, or 2. Double Fat Suppression (DFS) pulses if one wishes not to calculate TI1 and TI2. DFS combines SPIR and CHESS pulses together with variable flip angles to effectively suppress fat signal (e.g., see published U.S. Patent Application No. US 2010/0194388 A1).

Readout can use:

1. bSSFP (balanced Steady State Free Precession)
2. GRE (GRadient Echo).

The exemplary embodiments provide better fat suppression performance than STIR, SPIR and CHESS in LGE. They also can be used in both 1.5 T and 3.0 T MRI gantries.

The first exemplary embodiment can invert and null water signal and fat signal separately (while the prior art inverted both fat and water signals together, which makes it hard to separate infarcted myocardium and fat because both have short T1).

The second exemplary embodiment can suppress fat signal effectively if the first inversion pulse is non-selective.

In summary, exemplary embodiments provide two LGE MI fat suppression methods for separately nulling each of normal and fat tissue NMR responses during an active MRI data acquisition portion of an MRI data acquisition sequence:

a. Water only excitation/inversion followed by fat suppression pulse just before the LGE acquisition. Water inversion can be realized by either composite RF pulses or a water excitation pulse. The following fat suppression can use fat selective CHESS, fat selective SPIR, or double FatSat.

b. If a conventional non-selective inversion pulse is to be used, more effective fat suppression pulses can be effected by using variable flip angle CHESS/SPIR techniques to also suppress fat signal data acquisition time.

The first method (method a) can invert water signal and fat signal separately in LGE MI MRI, thus both healthy myocardium and fat signal can be nulled and substantially only infarct myocardial signal is acquired. The second method (method b) can suppress fat signal effectively if a non-selective pulse is chosen for the first IR pulse by also managing to null the fat signal at data acquisition time.

The following calculations show an exemplary calculation for tau for the composite RF pulse used in embodiment 1 (method a).

Since the chemical shift difference between water and fat is 3.5 ppm (parts per million) so at 1.5 T, the frequency difference $\Delta f$ between fat and water is:

$\Delta f = 3.5 \text{ ppm} \times f$, where $f = \gamma/2\pi \times Bo, \gamma/2\pi$ is gyromagnetic ratio $\Delta f = 3.5 \times 10^{-6} \times 42.576 \text{ Hz/T} \times 10^6 \times Bo = 149.016 \text{ Hz/T} \times Bo$ At $Bo=1.5$ T, $\Delta f = 149.016$ Hz/T × 1.5 T = 224 Hz At $Bo=3.0$ T, $\Delta f = 149.016$ Hz/T × 3.T = 447 Hz.

Fat protons precess faster than water protons, so the minimum time for fat signal and water signal to have opposite phase is:

tau = $0.5/\Delta f$

At $Bo=1.5$ T, tau = 0.5/(224 Hz) = 2.2 ms

At $Bo=3.0$ T, tau = 0.5/(447 Hz) = 1.1 ms

The following calculations show exemplary calculations for TI1 and TI2 (at 1.5 T) in embodiment 1 (method a) and embodiment 2 (method b) respectively, if using SPIR to invert the fat signal.

At 1.5 T, if one assumes the healthy myocardium $T1_h$ (spin-lattice relaxation time) is ~1000 ms, the fat $T1_f$ is ~200 ms, then the inversion time (TI) between the inversion point and the null point is $TI_h = T1_h \times \ln 2 = 693$ ms for healthy myocardium and $TI_f = 139$ ms for fat.

So in method (a), TI2=$TI_f$=139 ms, TI1=$TI_h$−TI2=693−139=554 ms; the TI2 value can be specified by the users, or empirical values may be employed if not user-specified.

In method (b), TI1+TI2=$TI_h$, −1−2exp(−TI1/$T1_f$)=1−2exp[(TI2−$TI_f$)/$T1_f$], if the above two equations are solved, TI1 and TI2 can be calculated. Using the assumed values at 1.5 T, TI1=566 ms and TI2=127 ms.

Figure 5:
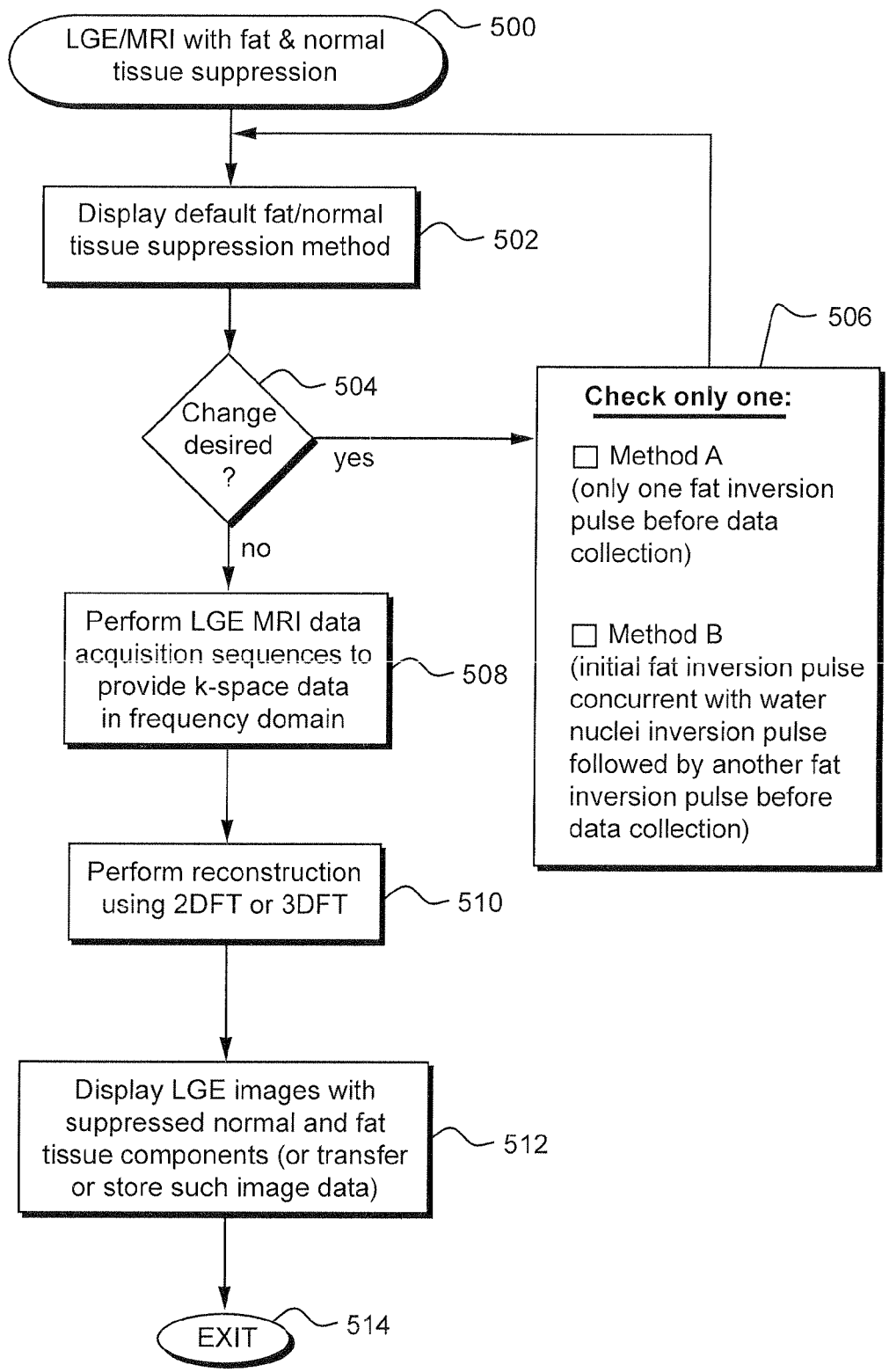
FIG. 5 is a schematic illustration of exemplary computer program code structure in the form of a flow chart for implementing an exemplary embodiment of LGE MRI data acquisition/reconstruction/display of images with fat and normal myocardial tissue suppression.

As shown in FIG. 5, an exemplary LGE MRI data acquisition sequence with fat and normal tissue suppression is entered at 500. At 502, default fat/normal tissue suppression method parameters may be depicted and, if desired, as detected at step 504, then control may be passed for operator modification of such parameters at step 506 before the modified parameters are again displayed at 502. As will be understood by those in the art, the normal data acquisition sequence parameters in addition to the new ones depicted herein may also be modified by the operator in accordance with conventional practice.

After the desired fat and normal tissue suppression methodology has been approved, control is passed to step 508 in FIG. 5. Here, a modified LGE MRI data acquisition sequence is repeatedly performed so as to provide sufficient k-space data in the frequency domain—in accordance with either method (a) or method (b) as depicted in the exemplary embodiments, for example, at FIGS. 3 and 4, respectively.

Once sufficient k-space data has been acquired, then conventional 2DFT or 3DFT reconstruction is performed at step 510 followed by display of the acquired LGE image data with suppressed normal and fat tissue components at 512. Of course, as those in the art will understand, instead of immediate display, the LGE image data may be transferred to another location and/or stored for display later or elsewhere. The LGE MRI with fat and normal tissue suppression sub-routine is exited at 514 and control is passed back to the higher level subroutine calling operating system or the like, as will be appreciated by those in the art.

While certain embodiments of the invention have been described, these embodiments have been presented by way of example only, and are not intended to limit the scope of the invention. Indeed, the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. A magnetic resonance imaging (MRI) system comprising:
    an MRI gantry having static and gradient magnet assemblies and at least one radio frequency (RF) coil defining an image volume into which a patient region of interest (ROI) can be disposed;
    MRI control circuits connected to control components within said MRI gantry and configured to effect MRI data acquisition sequences of RF and gradient magnetic pulses which elicit MRI signals from patient tissue when an ROI is disposed therein, to acquire and process said elicited MRI signals into MR image data;
    said MRI control circuits being configured to:
        (a) acquire k-space data of a patient ROI during an MRI data acquisition sequence including a nuclear magnetic resonance (NMR) signal readout period, said MRI data acquisition sequence using at least one water-specific RF NMR magnetization inversion pulse, a first fat-specific inversion pulse and at least one second fat-specific RF NMR magnetization inversion pulse imposed prior to said readout period, said at least one water-specific inversion pulse and said at least one second fat-specific inversion pulse each being respectively timed to cause a substantial null in NMR magnetization of fat tissue protons inverted by the at least one second fat-specific RF NMR magnetization inversion pulse and a substantial null in NMR magnetization of normal tissue protons inverted by the water-specific RF NMR magnetization inversion pulse to occur during said readout period when MRI data in a center portion of k-space is being acquired;
        (b) process said acquired k-space data into MR image data in the spatial domain; and
        (c) store, transfer and/or display said processed MR image data, with the processed MR image data representing a contrast enhanced image of tissues within the ROI but having substantially suppressed normal and fat nuclei components therein.

2. An MRI system as in claim 1 wherein said MRI control circuits are configured to use a late gadolinium enhanced (LGE) data acquisition sequence including at least one fat-specific RF NMR magnetization inversion pulse imposed (i) after a water-specific RF NMR magnetization inversion pulse timed to cause a substantial null in NMR magnetization of normal tissue protons during said readout period when MRI data for a center portion of k-space is being acquired and (ii) before MRI data for a center portion of k-space is acquired, which fat-specific inversion pulse is also timed to cause a substantial null in NMR magnetization during said readout period when MRI data for a center portion of k-space is being acquired.

3. An MRI system as in claim 2, wherein said MRI control circuits are configured to also impose an initial fat-specific inversion pulse substantially concurrent with imposition of said water-specific RF NMR magnetization inversion pulse.

4. An MRI system as in claim 2, wherein said patient ROI includes myocardium and wherein said contrast enhanced image depicts substantially only infarct myocardium.

5. An MRI system as in claim 3 wherein said patient ROI includes myocardium and wherein said contrast enhanced image depicts substantially only infarct myocardium.

6. A magnetic resonance imaging (MRI) method, with the acquiring, processing and storing, transferring and/or displaying steps being performed with a magnetic resonance imaging system, comprising:
    acquiring k-space data of a patient ROI during an MRI data acquisition sequence including a nuclear magnetic resonance (NMR) signal readout period, said MRI data acquisition sequence using at least one water-specific RF NMR magnetization inversion pulse, a first fat-specific inversion pulse and at least one second fat-specific RF NMR magnetization inversion pulse imposed thereafter, said water-specific inversion pulse and the at least one second fat specific inversion pulse each being respectively timed to cause a substantial null in NMR magnetization of fat tissue protons inverted by the at least one second fat-specific RF NMR magnetization inversion pulse and a substantial null in NMR magnetization of normal tissue protons inverted by the water-specific RF NMR magnetization inversion pulse to occur during said readout period when MRI data in a center portion of k-space is being acquired;
    (b) processing said acquired k-space data into MR image data in the spatial domain; and
    (c) storing, transferring and/or displaying said processed MR image data, with the processed MR image data representing a contrast enhanced image of tissues within the ROI but having substantially suppressed normal and fat nuclei components therein.

7. An MRI method as in claim 6 wherein said data acquisition sequence comprises a late gadolinium enhanced (LGE) data acquisition sequence including at least one fat-specific RF NMR magnetization inversion pulse imposed (i) after a water-specific RF NMR magnetization inversion pulse timed to cause a substantial null in NMR magnetization of normal tissue protons during said readout period when MRI data for a center portion of k-space is being acquired and (ii) before a time said readout period when MRI data for a center portion of k-space is being acquired, which fat-specific inversion pulse is also timed to cause a substantial null in NMR magnetization during said readout period when MRI data for a center portion of k-space is being acquired.

8. An MRI method as in claim 7, wherein an initial fat-specific inversion pulse is imposed substantially concurrent with imposition of said water-specific RF NMR magnetization inversion pulse.

9. An MRI method as in claim 7, wherein said patient ROI includes myocardium and wherein said contrast enhanced image depicts substantially only infarct myocardium.

10. An MRI system as in claim 8 wherein said patient ROI includes myocardium and wherein said contrast enhanced image depicts substantially only infarct myocardium.

* * * * *